United States Patent [19]

Stine

[11] Patent Number: 4,594,073
[45] Date of Patent: Jun. 10, 1986

[54] ASPIRATION SYRINGE HOLDER

[76] Inventor: Charles R. Stine, 5779 Chipmunks Run, Apt. A, Indianapolis, Ind. 46254

[21] Appl. No.: 666,929

[22] Filed: Oct. 31, 1984

[51] Int. Cl.⁴ ............................................. A61M 1/00
[52] U.S. Cl. .................................. 604/187; 604/232; 128/765
[58] Field of Search ............... 604/187, 407, 208–210, 604/223–224, 232, 233, 316; 128/765; 141/27

[56] References Cited

U.S. PATENT DOCUMENTS

| | | | |
|---|---|---|---|
| 375,427 | 12/1887 | Richards | 433/81 |
| 2,892,457 | 6/1959 | Sturtz | 604/223 |
| 3,040,744 | 6/1962 | Hoggard | 128/765 |
| 3,606,085 | 8/1969 | Spilman | 222/43 |
| 3,819,091 | 6/1974 | Hollender | 604/223 X |
| 4,022,207 | 5/1977 | Citrin | 604/209 |
| 4,231,368 | 11/1980 | Becker | 604/157 |
| 4,263,911 | 4/1981 | McCormack et al. | 604/227 |
| 4,357,971 | 11/1982 | Friedman | 604/218 |

*Primary Examiner*—Dalton L. Truluck
*Attorney, Agent, or Firm*—Woodard, Weikart, Emhardt & Naughton

[57] ABSTRACT

An aspiration syringe holder for use in fine needle aspiration is disclosed which includes a holder body for receiving and holding the syringe. Attached to the rear end of the holder body proximate the rear end of the syringe is a handle which extends outwardly therefrom. A trigger is mounted in longitudinal sliding engagement with the holder body and is manually movable from proximate the front end of the syringe rearwardly. A linkage connects the trigger to the syringe piston for transmitting the rearward movement of the trigger to the syringe piston.

12 Claims, 16 Drawing Figures

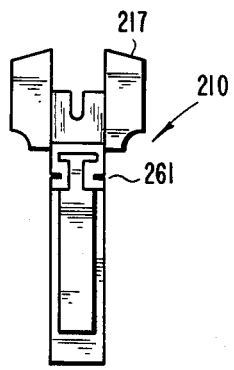
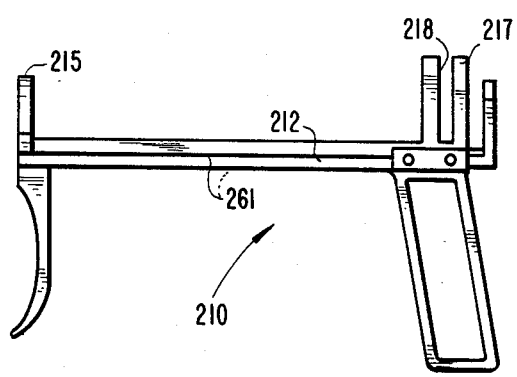
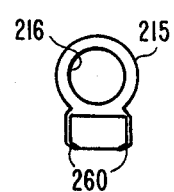
Fig.12  Fig.11  Fig.13
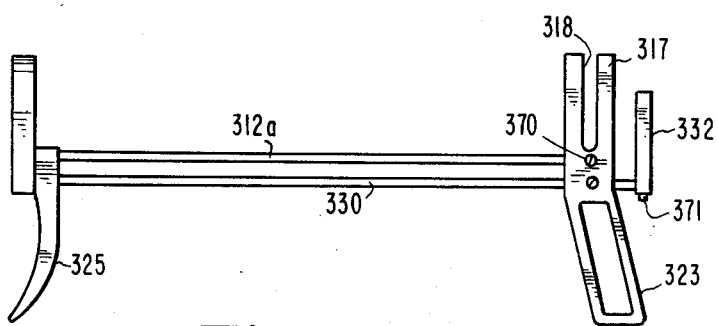
Fig.14
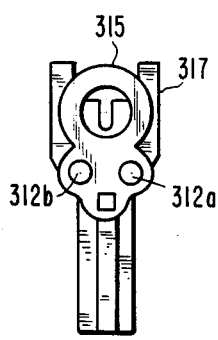
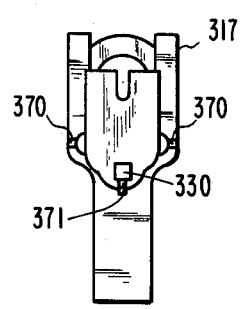
Fig.15  Fig.16

ASPIRATION SYRINGE HOLDER

BACKGROUND OF THE INVENTION

1. Field of the Invention

This invention relates generally to appliances for use with syringes and in particular to an aspiration syringe holder used with a syringe and needle for fine needle aspiration of tissue samples.

2. Background of the Prior Art

Cancer and other diseases involving cellular abnormality are best diagnosed by examination of tissue samples taken from the suspected area of the body. In the past, such tissue samples have been obtained by exploratory surgery or by relatively large-bore biopsy needles, both methods involving removal of relatively large tissue samples and involving significant trauma to tissues surrounding the area of interest. Because of their intrusive and disruptive nature, these methods of obtaining tissue samples carry the risk of spreading any cancerous cells that may be present throughout the surrounding tissues.

In recent years, advances in the field of cytology have made it possible to diagnose disease with very small tissue samples, such as might be gathered by aspiration into a fine hypodermic needle. Consequently, to take advantage of these cytological advances and to reduce the risks inherent in the prior methods, there has been rapid growth in the use of fine needle aspiration techniques. Such techniques typically involve an ordinary disposable plastic medical syringe having a small gauge needle attached. The empty syringe with its piston fully pushed in is manipulated to insert the needle into the patient's body until the tip of the needle is embedded in the tissue from which a sample is to be taken. The body of the syringe is held in place while the piston is withdrawn, causing a negative pressure in the needle, thereby aspirating a small sample of cells into the bore of the needle. As used here, negative pressure means less than ambient atmospheric pressure. Usually the sample will not be drawn into the syringe itself. The needle, with syringe attached, may then be withdrawn from the patient's body, with the sample later to be expelled onto a glass slide for cytological examination.

An appliance for use with a standard syringe and needle is shown in U.S. Pat. No. 3,819,091 to Hollender, issued June 25, 1974. The Hollender appliance enables the physician to insert the needle and aspirate the sample with one hand, thereby freeing his other hand to palpate and stabilize the area to be sampled. Hollender shows a first member which captively engages the flanges at the rear end of a standard syringe and a pair of rails extending rearwardly from the first member and terminating at a pistol grip type handle. A second member located between the first member and the pistol grip handle is configured to slide therebetween on the pair of rails. The second member captively engages the flange of the syringe piston and is configured to receive one or more human fingers. The pistol grip is used to manipulate and push the syringe to insert the needle into the patient's body. Once so inserted, the second member is drawn rearwardly with the fingers to aspirate the sample.

A disadvantage of the Hollender device is that the appliance is located almost entirely rearward of the syringe. Thus, the physician's hand is a relatively great distance from the tip of the needle. The present invention enables the physician's hand to be located much closer to the front of the syringe, thereby affording greater control over the placement and manipulation of the needle.

SUMMARY OF THE INVENTION

An aspiration syringe holder for holding a disposable type syringe having a piston and needle and for facilitating the use of such syringes in fine needle aspiration of tissue for cytological examination, includes a syringe holder body adapted and configured to receive and hold a disposable syringe. A handle is affixed to the syringe holder body and extends outwardly therefrom proximate the rear end of the syringe. A trigger extends outwardly from the syringe holder body forward of the handle and is manually movable from a position proximate the front end of said syringe rearwardly toward the rear end of said syringe in sliding engagement with the syringe holder body. A linkage is attached to the trigger and is adapted and configured to engage the piston of the syringe for transmitting the rearward motion of the trigger to the piston.

It is an object of the invention to provide an improved aspiration syringe holder which permits the physician's hand to be located close to the needle of the syringe for improved control.

Further objects and advantages of the invention will become apparent from the following description.

BRIEF DESCRIPTION OF THE DRAWINGS

FIG. 11 is a left side elevational view of a second alternative embodiment of an aspiration syringe holder, in accordance with the present invention.

FIG. 12 is a front elevational view of the aspiration syringe holder of FIG. 11, with the forward ring removed.

FIG. 13 is a front elevational view of the forward ring of the aspiration syringe holder of FIG. 11.

FIG. 14 is a left side elevationsl view of a third alternative embodiment of an aspiration syringe holder, in accordance with the present invention.

FIG. 15 is is a front elevational view of the aspiration syringe holder of FIG. 14.

FIG. 16 is a rear elevational view of the aspiration syringe holder of FIG. 14.

DESCRIPTION OF THE PREFERRED EMBODIMENT

Figure 1:
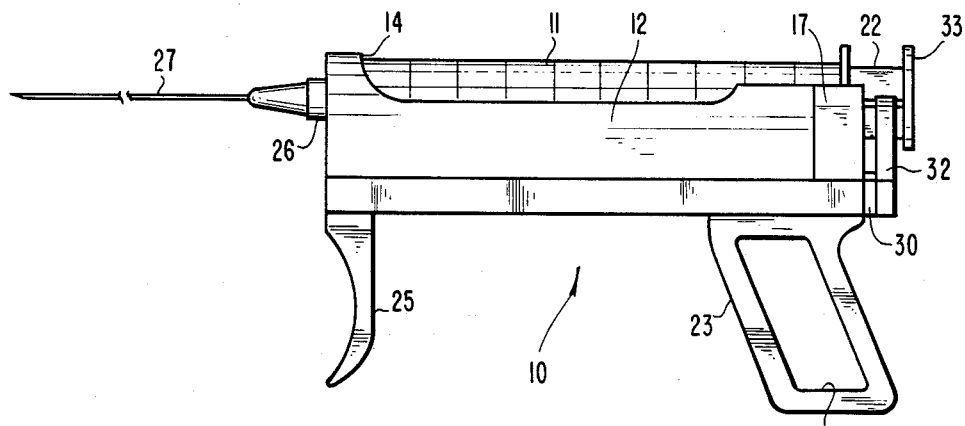
FIG. 1 is a side elevational view of an aspiration syringe holder made in accordance with the present invention, shown holding a disposable type syringe and needle.
Figure 2:
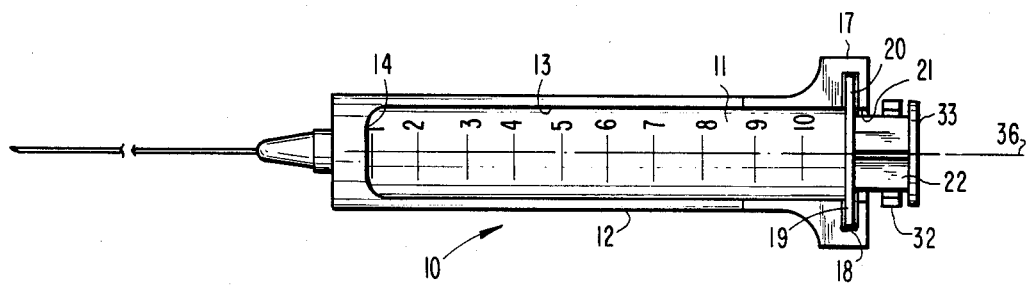
FIG. 2 is a top view of the aspiration syringe holder of FIG. 1.
Figure 3:
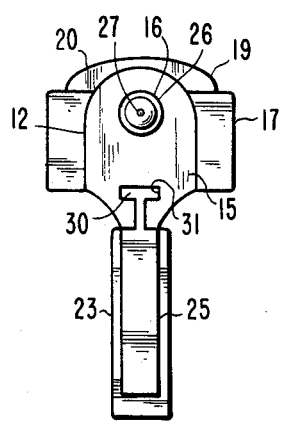
FIG. 3 is a front elevational view of the aspiration syringe holder of FIG. 1.

Referring in particular to FIGS. 1 and 2, there is illustrated an aspiration syringe holder 10, shown holding a standard disposable plastic 10 cc (ten cubic centimeter) syringe 11. Holder 10 as shown is configured to fit a Beckton-Dickenson brand syringe, although the invention described herein may be readily used with other brands of syringes by merely modifying the dimensions of the aspiration syringe holder, as would be readily apparent to those skilled in the art. Aspiration syringe holder 10 includes a holder body 12 for receiving and holding syringe 11. Holder body 12 is an elongated member of approximately the same length as syringe 11, and is provided with a longitudinal open-topped channel 13 having a transversely arcuate bottom of a radius selected to provide a snug fit with syringe 11. The front end of holder body 12 is provided with a lip 14 which bridges channel 13 and in combination therewith forms a short conical cylindrical recess into which the tapered front end of syringe 11 snugly fits. As is shown best in FIGS. 3 and 6, front wall 15 of holder body 12 forms a stop to prevent syringe 11 from being displaced longitudinally forward. An aperture 16 is provided in front wall 15 through which the Luer lock connector 26 and needle 27 of syringe 11 extend. Referring again to FIGS. 1 and 2, the rear end of holder body 12 is provided with a widened portion 17 having an interior groove 18 configured to receive therein flanges 19 and 20 of syringe 11. Groove 18 is of a width calculated to provide a snug friction fit with flanges 19 and 20. The top edges of groove 18 are beveled (see FIG. 6) to aid in inserting flanges 19 and 20 therein. The rear end of widened portion 17 is provided with a semi-circular open-topped cutout 21 sized to provide clearance between portion 17 and syringe piston 22 which extends rearwardly through cutout 21.

Attached proximate the rear end of holder body 12 and extending downwardly therefrom is handle 23. In the preferred embodiment, handle 23 is provided with a cutout portion 24. Cutout portion 24 is provided primarily to reduce weight and save material costs.

Proximate the front end of holder body 12 and extending downwardly therefrom is trigger 25. Trigger 25 is attached to a T-shaped rail 30 which is disposed within a corresponding T-shaped longitudinal slot 31 (see FIGS. 3 and 6) in the bottom of holder body 12 in longitudinal sliding engagement therewith such that trigger 25 can be slid rearwardly toward handle 23. T-shaped slot 31 extends the full length of holder body 12 and is open at both ends. Attached to the rear end of T-shaped rail 30 is a vertically oriented piston plate 32 which is configured to engage the front side of flange 33 of syringe piston 22.

Figure 4:
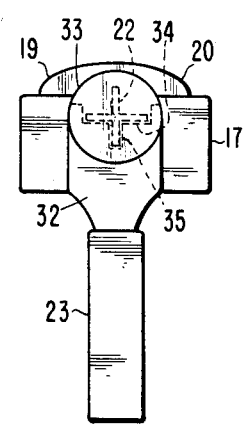
FIG. 4 is a rear elevational view of the aspiration syringe holder of FIG. 1.
Figure 5:
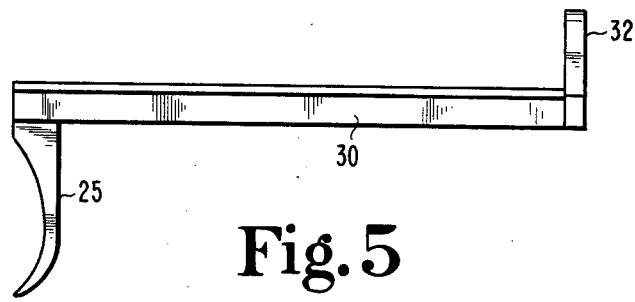
FIG. 5 is a side elevational view of the trigger, sliding rail and piston plate of the aspiration syringe holder of FIG. 1.

Referring to FIG. 4, it can be seen that piston plate 32 is provided with cutout 34 and slot 35 for receiving therein syringe piston 22 which is X-shaped in cross section. FIG. 5 illustrates the linkage formed by trigger 25, T-shaped rail 30 and plate 32 as removed from aspiration syringe holder 10, showing the relationship of these parts more clearly. As trigger 25 is slid rearwardly, the rearward motion is transmitted by T-shaped rail 30 and piston plate 32 to flange 33, resulting in the rearward movement of syringe piston 22 which causes negative air pressure within syringe 11 and needle 27.

In the preferred embodiment, aspiration syringe holder 10 is made of an injection molded plastic which is capable of withstanding autoclave sterilization. The preferred plastic is manufactured by General Electric Co. and sold under the trade name Valox. In the preferred embodiment, the Valox plastic is mixed with about 15% randomly oriented fiberglass fibers.

Figure 6:
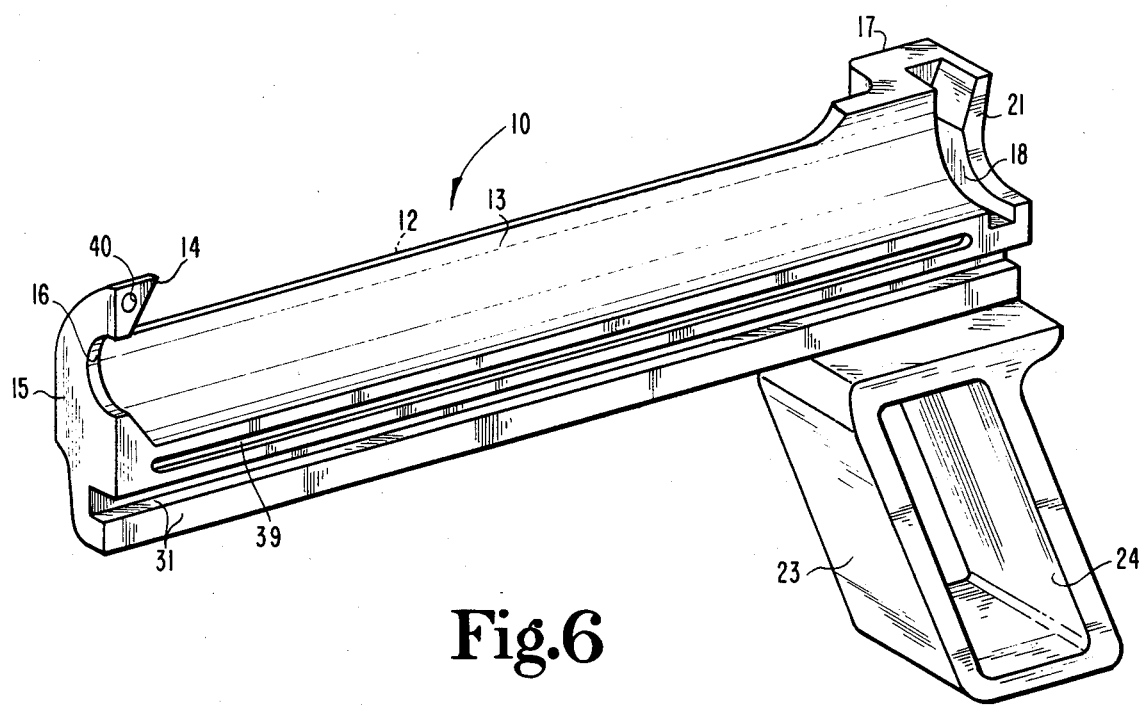
FIG. 6 is a perspective view of the handle and right half of the holder body of the aspiration syringe holder of FIG. 1, shown prior to assembly.
Figure 7:
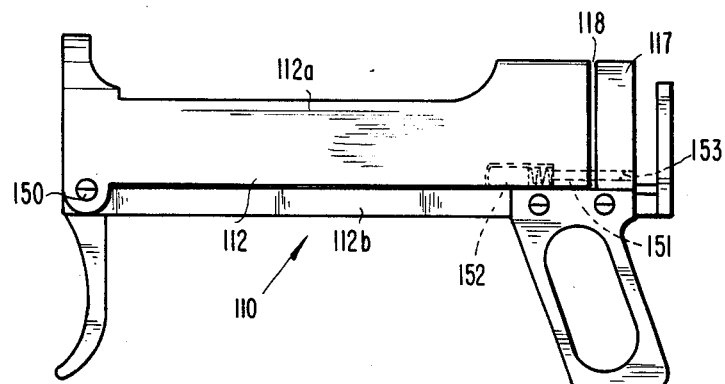
FIG. 7 is a left side elevational view of an alternative embodiment of an aspiration syringe holder, in accordance with the present invention.
Figure 8:
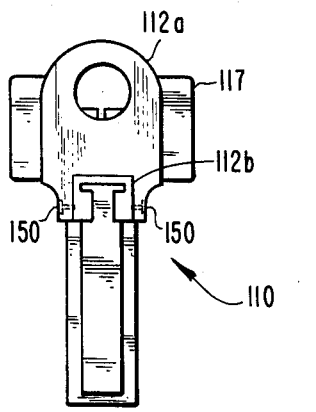
FIG. 8 is a front elevational view of the aspiration syringe holder of FIG. 7.
Figure 9:
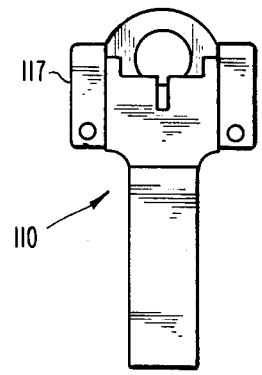
FIG. 9 is a rear elevational view of the aspiration syringe holder of FIG. 7.

Referring in particular to FIG. 6, there is shown one half of the holder body prior to assembly. Holder body 12 is molded as two pieces, the plane of separation being vertical plane 36 (shown in FIG. 2) which bisects holder body 12 and T-shaped slot 31 into right and left halves. Handle 23 is not bisected, but rather is molded integrally with the right half. Trigger 25, T-shaped rail 30 and piston plate 32 are molded integrally as a third piece. During assembly, the third piece is sandwiched between the right and left halves within T-shaped slot 31 which is defined by the assembled halves. The right and left halves are secured together with a suitable cement, care being taken not to introduce cement into T-shaped slot 31. To aid in alignment and connection of the right and left halves during assembly, the right half is provided with groove 39 and hole 40, which mate with a corresponding tongue and pin molded on the left half.

Use of aspiration syringe holder 10 for fine needle aspiration would typically involve the following procedure. Syringe 11, with syringe piston 22 fully pushed in, is installed into holder body 12 by inserting the Luer lock connector 26 (with or without a needle of suitable length and gauge attached) through aperture 16 in front wall 15. The rear end of syringe 11 is then lowered into channel 13 with flanges 19 and 20 fitting snugly into groove 18. When so installed, syringe 11 is held securely against longitudinal and horizontal displacement with respect to holder body 12. The front of the syringe is held against vertical displacement by lip 14 and by aperture 16 which engages Luer lock connector 26. The rear of syringe 11 is held against vertical displacement by friction between flanges 19 and 20 and groove 18, but syringe 11 may still be easily removed by supplying sufficient upward force to the rear end to overcome the friction fit. During installation of syringe 11 into holder body 12, it is important that piston plate 32 be located forward of flange 33 of syringe piston 22. It may be necessary to rotate syringe 11 so that X-shaped piston 22 can be received within cutout 34 and slot 35 of piston plate 32.

Aspiration syringe holder 12, with syringe and needle installed, can be held by the physician in one hand with handle 23 between his thumb and palm, and with his index finger extending along the side of holder body 12. The second (and perhaps third) finger of the same hand can be used to manipulate the trigger. The above described holding method affords the physician great control over the placement and manipulation of the needle, as he is in effect pointing his index finger where he wants the needle to go. The physician's other hand is free to palpate and stabilize the area of the patient's body into which the needle is to be inserted. Before inserting the needle into the body, the trigger should be in a forward position. It need not, however, be positioned all the way forward. In fact, the trigger will be easier to manipulate by those with small hands if it is initially positioned somewhat rearward of its forwardmost position so that it can be reached comfortably with the second finger.

Once the needle has been inserted into the tissue of interest, it is relatively easy to hold aspiration syringe holder 10 steady while trigger 25 is pulled back to aspirate the sample into the bore of the needle. When blood or other material appears in the translucent plastic hub of the needle, the physician is assured that a sample has been obtained. Once the sample has been aspirated, the trigger should be released to allow the syringe plunger to return to equilibrium before removing the needle from the body. When released, trigger 25 automatically returns forward due to the differential between atmospheric pressure and the negative pressure inside the syringe acting on syringe plunger 22. Equalizing the pressure within and without the syringe ensures that the sample will remain within the bore of the needle instead of being sucked into the syringe by an inrush of air when the needle tip clears the body. The needle containing the sample can be withdrawn from the body by pulling the aspiration syringe holder rearward.

The sample can be removed from the needle by removing the needle from the syringe, drawing air into the syringe, reattaching the needle and expressing the sample from the needle by forcing the plunger forward. Alternatively, the needle could be attached to a second syringe for expressing the sample.

Another embodiment of the present invention is illustrated in FIGS. 7-10. Shown is an aspiration syringe holder 110 including a syringe holder body 112 which is comprised of an upper portion 112a and a lower portion 112b which are pivotally connected together at the front of syringe holder body 112 by pivot screws 150. A rear portion 117 is attached to and extends upwardly from lower portion 112b rearwardly of upper portion 112a. Upper portion 112a and rear portion 117 are spaced apart to define a groove 118 between them. The flanges of the syringe are received within groove 118. Upper portion 112a is provided with a locking pin 151 which is biased rearwardly by spring 152. Locking pin 151 engages bore 153 in rear portion 117 to lock upper portion 112a in place to prevent its pivoting about pivot 150.

Figure 10:
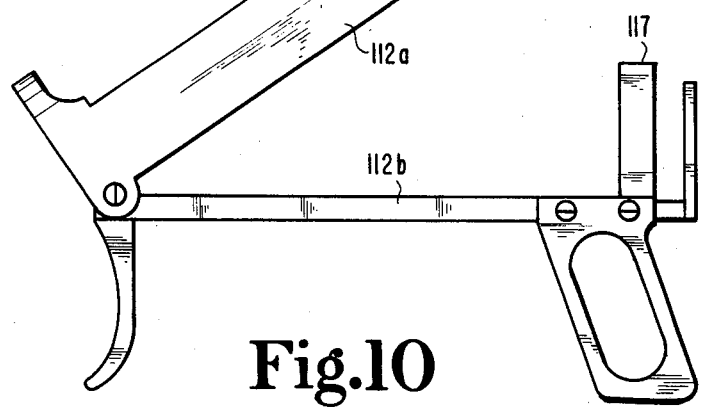
FIG. 10 is a left side elevational view of the aspiration syringe holder of FIG. 7, particularly showing the syringe holder body in its loading position.

To insert the syringe into aspiration syringe holder 110, upper portion 112a is first pivoted into an upward orientation, as shown in FIG. 10. The syringe can be easily inserted into upper portion 112a, which is then lowered until locking pin 151 snaps into bore 153. The flanges of the syringe will be sandwiched between upper portion 112a and rear portion 117 within groove 118. Aspiration syringe holder 110 is otherwise operated similarly to aspiration syringe holder 10, described above.

Another variation of the present invention is shown in FIGS. 11-13. Illustrated is aspiration syringe holder 210 having a syringe holder body 212 which includes a forward ring 215 (shown best in FIG. 13) having an aperture 216 through which the Luer lock needle connector fits. Alternatively, aperture 216 could be made larger so that it would fit about the front portion of the barrel of the syringe. The longitudinal position of ring 215 is adjustable by sliding it forward or rearward, thereby accommodating syringes of various lengths. Tongues 260 of ring 215 engage longitudinal grooves 261 which are located on both sides of holder body 212. Rear portion 217 is provided with a groove 218 for receiving the flanges of the syringe.

Yet another embodiment of the present invention is illustrated in FIGS. 14-16. In this embodiment, the holder body includes a pair of rails 312a and 312b connecting the forward ring 315 to the rear portion 317. Trigger 325 is mounted so that it slides on rails 312a and 312b. Rear portion 317, including groove 318 for receiving the syringe flanges, is integral with handle 323. The rear portion 317—handle 323 combination is slidable upon rails 312a and 312b, with setscrew 370 being provided to lock them at a selected location. Similarly, piston plate is slidable upon linkage rail 330, with setscrew 371 being provided to lock it at a selected location. Thus, the position of rear portion 317 and the length of linkage rail 330 can be adjusted for syringes of various lengths.

While particular embodiments of the invention have been illustrated and described in detail in the drawings and foregoing description, it is to be understood that this description is made only by way of example and not as a limitation to the scope of the invention which is claimed below.

The invention claimed is:

1. An aspiration device comprising:
    a syringe of the disposable type having an open rear end, flanges extending transversely therefrom, a piston extending rearwardly from the open rear end of said syringe, said piston having a rear flange, and a needle removably attached to the front end of said syringe; and
    an aspiration syringe holder for facilitating the use of said syringe in fine needle aspiration of tissue for cytological examination, said aspiration syringe holder comprising:
    a syringe holder body having means for receiving and holding said disposable type syringe:
    a handle affixed to said syringe holder body and extending outwardly therefrom proximate the rear end of said syringe, said handle having a rear surface configured for engagement with the palm of a human operator and arranged for applying to said syringe holder body forwardly directed force applied by said human operator to the rear surface of said handle, the rear surface of said handle being located forwardly of the rearwardmost excursion of the piston of said syringe;
    a trigger extending outwardly from said syringe holder body forward of said handle;
    means for maintaining said trigger in sliding engagement with said holder body such that said trigger is manually movable from a position proximate the front end of said syringe rearwardly toward the rear end of said syringe in sliding engagement with said syringe holder body; and
    a linkage attached to said trigger and adapted and configured to engage the piston of said syringe for transmitting the rearward motion of said trigger to the piston, thereby moving the piston rearwardly with respect to said syringe.

2. The aspiration device of claim 1, wherein the means for receiving and holding said syringe includes a forward means for captively engaging the front portion of said syringe and a rearward means for captively engaging the transverse flanges of said syringe.

3. The aspiration device of claim 2, wherein the rearward means includes a groove for receiving therein the transverse flanges of said syringe.

4. The aspiration device of claim 3, wherein said linkage includes a piston plate configured to engage the front surface of the rear flange of said syringe piston.

5. The aspiration device of claim 4, wherein said syringe holder body includes a longitudinal channel having a transversely arcuate bottom for receiving the barrel of said syringe.

6. The aspiration device of claim 5, wherein said linkage includes a rail and said syringe holder body includes a longitudinal slot, the rail being disposed within said slot in sliding engagement therewith.

7. The aspiration device of claim 6, wherein the rail of said linkage and the longitudinal slot of said syringe holder body are T-shaped in cross-section.

8. The aspiration device of claim 4, wherein said syringe holder body includes an upper and a lower portion pivotably connected together proximate the front of said syringe holder body, and further including a rear portion extending from the lower portion and located rearwardly of the upper portion, the upper portion and the rear portion being spaced apart to define therebetween the groove for receiving the transverse flanges of said syringe.

9. The aspiration device of claim 8, and further including releasable locking means for locking the upper portion of said syringe holder body against rotation about the pivotal connection with respect to the lower portion.

10. The aspiration device of claim 4, and further including means for adjusting the longitudinal position of the forward means for captively engaging the front portion of said syringe, to accommodate syringes of various lengths.

11. The aspiration device of claim 4, and further including means for adjusting the longitudinal position of the rearward means for captively engaging the transverse flanges of said syringe, and means for adjusting the length of said linkage, to accommodate syringes of various lengths.

12. The aspiration device of claim 11, wherein said syringe holder body includes a pair of tails connecting the forward means for captively engaging the front portion of said syringe to the rearward means for captively engaging the transverse flanges of said syringe, said trigger being in sliding engagement with the pair of rails.

* * * * *